United States Patent [19]

Maki et al.

[11] Patent Number: 4,613,700

[45] Date of Patent: Sep. 23, 1986

[54] PROCESS FOR PRODUCING AROMATIC ALDEHYDES

[75] Inventors: Takao Maki, Kanagawa; Toshiharu Yokoyama, Tokyo, both of Japan

[73] Assignee: Mitsubishi Chemical Industries Limited, Tokyo, Japan

[21] Appl. No.: 692,475

[22] Filed: Jan. 18, 1985

[30] Foreign Application Priority Data

Jan. 18, 1984 [JP] Japan ................................... 59-6967
May 17, 1984 [JP] Japan ................................. 59-98979

[51] Int. Cl.$^4$ ............................................. C07C 45/41
[52] U.S. Cl. ..................................... 568/435; 502/308;
502/324; 502/325; 502/338; 502/340; 502/349
[58] Field of Search ......................................... 568/435

[56] References Cited

U.S. PATENT DOCUMENTS 4,093,661  6/1978  Trecker et al. ................ 568/435 X
4,328,373  5/1982  Strojny ................................ 568/435

*Primary Examiner*—Bernard Helfin
*Attorney, Agent, or Firm*—Sughrue, Mion, Zinn, Macpeak, and Seas

[57] ABSTRACT

An improved process for catalytic hydrogenation of aromatic carboxylic acids to produce aromatic aldehydes is described, using a catalyst comprising zirconium oxide containing as an essential component at least one element selected from the group consisting of chromium, manganese, iron, cobalt, zinc, bismuth, lead, rhenium and the elements of Group III of periods 3 to 6 of the periodic table; the process results in improved catalyst activity and produces the desired aromatic aldehydes in high yield.

8 Claims, No Drawings

PROCESS FOR PRODUCING AROMATIC ALDEHYDES

FIELD OF THE INVENTION

The present invention relates to a process for producing aromatic aldehydes by hydrogenation of aromatic carboxylic acids.

BACKGROUND OF THE INVENTION

Several attempts have been made to produce aromatic aldehydes by hydrogenation of aromatic carboxylic acids, but one great problem common to all of these attempts has been that only a low yield is obtained if general-purpose hydrogenation catalysts are used. U.S. Pat. No. 4,328,373 reports that benzaldehyde can be formed by hydrogenation of benzoic acid in the presence of a zirconium oxide catalyst. However, according to experiments conducted by the present inventors, if zirconium oxide prepared by conventional techniques is used as a catalyst, the high temperature that is necessary for the reaction is detrimental to the yield of the end product and the life of the catalyst.

SUMMARY OF THE INVENTION

Therefore, a primary object of the present invention is to provide a process for producing aromatic aldehydes by hydrogenation of aromatic carboxylic acids using a catalyst which overcomes the foregoing problems.

As a result of extensive investigations, it has now been found that the inclusion of one or more of certain additional elements as an essential component of the catalyst overcomes the foregoing problems.

Accordingly, the present invention is directed to a process for producing an aromatic aldehyde by catalytic hydrogenation of an aromatic carboxylic acid, wherein the improvement comprises using a catalyst comprising zirconium oxide containing as an essential component at least one element selected from the group consisting of chromium, manganese, iron, cobalt, zinc, bismuth, lead, rhenium and the elements of Group III in periods 3 to 6 of the periodic table.

The process of the present invention enables aromatic aldehydes to be produced in high yield over an extended period.

DETAILED DESCRIPTION OF PREFERRED EMBODIMENT

An important feature of the process of the present invention lies in using a zirconium oxide catalyst modified with at least one specified element selected from the group consisting of chromium, manganese, iron, cobalt, zinc, bismuth, lead, rhenium, and the elements of Group III in periods 3 to 6 of the periodic table. Suitable elements of Group III in periods 3 to 6 of the periodic table include aluminum, scandium, yttrium, gallium, indium and thallium, as well as lanthanoids such as lanthanum, cerium, praseodymium, neodymium, etc. The use of indium is particularly preferred. Zirconium oxide, which is the main component of the catalyst used in the process of the present invention, should preferably have high chemical purity and a porous structure. Such zirconium oxide may be prepared by baking high-purity zirconium hydroxide, zirconium carbonate, zirconyl nitrate, etc., at a suitable temperature typically in the range of from about 400° to 900° C. The activity of the catalyst used in the present invention is highly dependent on the properties of the zirconium oxide. Particularly preferred is such zirconium oxide that the acidity function (Ho) as measured by adsorption with Hammett indicator is greater than +4.0 and the volume of pores having radii not greater than 100 Å ($100 \times 10^{-7}$ mm) as measured by mercury porosimetry is 0.05 ml/g or more.

Various methods may be employed to modify the zirconium oxide shown above with the elements also specified hereinbefore. According to one method, zirconium oxide or a starting material therefor (i.e., zirconium hydroxide, carbonate, etc.) is impregnated or sprayed with a solution of a compound of the specified element. In a second method, generally referred to as the coprecipitation process, a compound of the specified element is caused to coprecipitate with a starting zirconium oxide material when the latter is precipitated from a soluble zirconium salt. A third method, named the kneading process, comprises mechanically mixing a compound of the specified element into zirconium oxide or a starting material therefor. Whichever method is used, the specified element may be added either before, during or after the preparation of the zirconium oxide. For example, the specified element may be mixed with the starting material of the zirconium oxide, and the mixture then baked to obtain a catalyst according to the present invention. In this case, it is highly likely that the specified element has converted itself to, for example, an oxide form.

The specified element is generally added in an atomic ratio with respect to the zirconium of from about 0.001/1 to 0.5/1, and preferably from 0.01/1 to 0.1/1. If zirconium oxide containing rhenium as the specified element is used directly as a catalyst, toluene and other products of excessive hydrogenation may be formed as by-products. In order to avoid this problem, the zirconium oxide may be further contain an alkali metal or alkaline earth metal such as lithium, sodium, potassium, rubidium, cesium, beryllium, magnesium, calcium, strontium or barium. Such alkali metals or alkaline earth metals may be added in an atomic ratio range with respect to the rhenium of from about 0.01/1 to 1.0/1, and preferably from 0.05/1 to 0.5/1.

Zirconium oxide containing the specified element is preferably formed into tablets or other suitable shapes or supported on inert carriers before being used as a catalyst.

Illustrative aromatic carboxylic acids that are used as the starting material in the process of the present invention include aromatic carboxylic acids and their esters. They are hydrogenated by the process of the present invention into aromatic aldehydes such as benzaldehyde, tolualdehyde, dimethylbenzaldehyde, butylbenzaldehyde, methoxybenzaldehyde, phenoxybenzaldehyde, hydroxybenzaldehyde, halobenzaldehyde and phthalaldehyde. These aromatic aldehydes are produced by hydrogenation of the corresponding aromatic carboxylic acids or esters thereof. The process of the present invention is advantageously used for producing benzaldehydes from benzoic acids.

The process of the present invention may be performed in either the vapor phase or the liquid phase. The hydrogenation reaction may be carried out in a fixed bed system with satisfactory results. The reaction temperature is generally selected in the range of from about 250° to 450° C., with the range of from 300° to 400° C. being preferred. At higher temperatures, the amount of by-product is increased, which results in deactivation of the catalyst. However, if zirconium oxide containing the specified element according to the present invention is used, a very interesting phenomenon often occurs in that even at elevated temperatures, smaller amounts of by-products are formed than in the case wherein unloaded zirconium oxide is used, and that as a result, the service life of the catalyst is extended. If the substrate for the reaction is a dialkyl or diaryl phthalate, an alkoxy carbonyl benzaldehyde or aryloxycarbonyl benzaldehyde is formed as an intermediate, and upon continued reaction, such intermediates are converted to phthalaldehyde. Several methods are available for increasing the yield of phthalaldehyde; one is to reduce the intermediate after separating the phthaladehyde, and in another method, the space velocity of the starting material is reduced sufficiently to ensure commmplete performance of the reaction. The reaction pressure is not critical for the present invention, but usually satisfactory results are achieved by performing the reaction at normal or slightly superatmosheric pressure. The space velocity of the aromatic carboxylic acids fed as the starting material is generally in the range of about 0.01 to 1 hr$^{-1}$, and preferably from 0.03 to 0.3 hr$^{-1}$, in terms of L.H.S.V. (liquid hourly space velocity). The space velocity of hydrogen generally ranges from about 100 to 10,000 hr$^{-1}$, and preferably is from 500 to 2,000 hr$^{-1}$, in terms of G.H.S.V. (gas hourly space velocity). The concentration of the aromatic carboxylic acid in the reaction system is generally in the range of from about 0.1 to 10 vol%, and preferably from 1 to 5 vol%, of hydrogen. Hydrogen need not be completely pure and may contain small amounts of inert gases such as nitrogen and water vapor.

The following examples are provided as a further illustration of the invention process, are not to be construed as limiting, and various modifications may be made thereto without departing from the spirit and scope of the present invention.

EXAMPLES 1 TO 9 AND COMPARATIVE EXAMPLES 1 AND 2

Zirconium oxide prepared by firing commercial zirconium hydroxide at 500° C. was pelletted into particles of 10 to 20 mesh. With these particles used as a catalyst, hydrogenation of benzoic acid was conducted under the following conditions.

Catalyst load: 13 ml
Reaction temperature: 350° C.
Reaction pressure: one atmosphere
Space velocity: benzoic acid: LHSV=0.07 hr$^{-1}$ hydrogen: GHSV=625 hr$^{-1}$ The results of the reaction on the second hour are shown in Table 1 as Comparative Example 1. Zirconium hydroxide of the same grade as used above was first impregnated with aqueous solutions of acetate salts of the elements listed in Table 1, and subsequently fired at 500° C. and shaped into particles of 10 to 20 mesh. The thus prepared catalysts were used in hydrogenating benzoic acid under the same conditions listed above. The results are also shown in Table 1 as Examples 1 to 9 and Comparative Example 2. The elements noted in Table 1 were added at an atomic ratio with respect to the zirconium of 0.05/1.

TABLE 1

| | Element added | Benzoic acid (%) conversion | Benzaldehyde (%) selectivity | Benzaldehyde space time yield (mol/kg-cat. hr) |
|---|---|---|---|---|
| Comparative Example 1 | none | 51.2 | 97.3 | 0.329 |
| Comparative Example 2 | B | 22.3 | 93.3 | 0.087 |
| Example 1 | Cr | 98.0 | 95.6 | 0.607 |
| Example 2 | Mn | 64.8 | 97.1 | 0.415 |
| Example 3 | Co | 84.8 | 98.6 | 0.506 |
| Example 4 | Nz | 99.3 | 84.7 | 0.577 |
| Example 5 | Bi | 58.3 | 97.9 | 0.349 |
| Example 6 | Pb | 100.0 | 80.0 | 0.416 |
| Example 7 | Y | 54.6 | 97.2 | 0.340 |
| Example 8 | Ce | 65.7 | 97.2 | 0.385 |
| Example 9 | In | 100.0 | 91.4 | 0.577 |

COMPARATIVE EXAMPLE 3

A 5% aqueous solution of zirconyl nitrate dihydrate was adjusted to pH 7 by dropwise addition of ammonia water. The resulting precipitate was filtered and washed with water. Following preheating at 130° C., the filter cake was fired at 600° C. to obtain zirconium oxide. After grinding the oxide into particles of 10 to 20 mesh, the particles were used as a catalyst in hydrogenating benzoic acid under the same conditions as used in Comparative Example 1. The results are shown in Table 2.

EXAMPLE 10

The procedure of Comparative Example 3 was repeated except that iron nitrate was added to the 5% aqueous solution of zirconyl nitrate dihydrate in such an amount that the atomic ratio of iron to zirconium was 0.05/1. The results of the reaction are shown in Table 2.

TABLE 2

| | Element added | Benzoic acid (%) conversion | Benzaldehyde (%) selectivity | Benzaldehyde space time yield (mol/kg-cat. hr) |
|---|---|---|---|---|
| Comparative Example 3 | none | 28.5 | 94.1 | 0.200 |
| Example 10 | Fe | 55.3 | 95.2 | 0.341 |

EXAMPLES 11 TO 17

Glass reaction tubes were packed with 5 ml each of catalysts having the compositions shown in Table 3. Under heating, the tubes were also charged with hydrogen and the aromatic carboxylic acids shown in Table 3. After performing hydrogenation of the aromatic carboxylic acids at the temperatures and for the periods listed in Table 3, the products were collected and analyzed. The results are shown in Table 3.

EXAMPLES 18 TO 25

Glass reaction tubes were packed with 5 ml each of catalysts having the compositions shown in Table 4. Under heating, the tubes were also charged with hydrogen and the aromatic carboxylic acid esters shown in Table 4. After performing hydrogenation of the aromatic carboxylic acid esters at the temperatures and for the periods listed in Table 4, the products were collected and analyzed. The results are shown in Table 4.

In Examples 11 to 25, those aromatic carboxylic acids having high melting points were fed into the reactors as solutions in benzene or xylene.

TABLE 3

| Example | X*1 | Catalyst (atomic ratio*2) | Solvent | H2 GHSV (hr−1) | Carboxylic acid LHSV (hr−1) | Temperature (C.°) | Length of run (hrs) | Carboxylic acid conversion (%) | Aldehyde selectivity (%) |
|---|---|---|---|---|---|---|---|---|---|
| 11 | p-(CH3)2CH | Cr—ZrO2 (5/100) | none | 1250 | 0.15 | 350 | 6.0 | 89 | 96 |
| 12 | " | Co—ZrO2 (5/100) | " | " | " | " | 2.5 | 51 | 85 |
| 13 | " | IN—ZrO2 (5/100) | " | " | " | 330 | 3.5 | 89 | 87 |
| 14 | " | Cs—Re—ZrO2 (0.2/1/100) | " | " | " | 300 | 4.5 | 44 | 71 |
| 15 | m-CH3O | Cr—ZrO2 (5/100) | " | " | 0.17 | 350 | 2.0 | 51 | 55 |
| 16 | 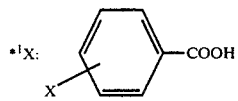 | Cr—ZrO2 (5/100) | xylene | 625 | 0.05 | " | 4.6 | 100 | 96 |
| 17 | m-Cl | Cr—ZrO2 (5/100) | benzene | " | " | " | 6.0 | 82 | 77 |

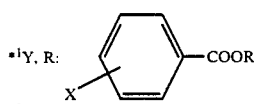

*2atomic ratio of specific element added with respect to the zirconium

TABLE 4

| Example | Y*1 | R*1 | Catalyst (atomic ratio*2) | Solvent | H2 GHSV (hr−1) | Carboxylic acid ester LHSV (hr−1) | Temperature (C.°) | Length of run (hrs) | Carboxylic acid ester conversion (%) | Aldehyde selectivity (%) |
|---|---|---|---|---|---|---|---|---|---|---|
| 18 | H | CH3 | Co—ZrO2 (5/100) | none | 1250 | 0.13 | 350 | 1.5 | 72 | 95 |
| 19 | " | " | In—ZrO2 (5/100) | " | " | 0.14 | 330 | 2.5 | 97 | 71 |
| 20 | " | " | Cs—Re—ZrO2 (5/100) | " | " | 0.13 | 300 | 3.5 | 27 | 60 |
| 21 | " | n-C4H4 | Cr—ZrO2 (5/100) | " | " | 0.20 | 330 | 4.0 | 82 | 93 |
| 22 | " | C6H5 | Cr—ZrO2 (5/100) | " | " | 0.22 | 350 | " | 97 | 98 |
| 23 | m-OH | CH3 | Cr—ZrO2 (5/100) | " | " | 0.17 | 400 | " | 76 | 42 |
| 24 | p-COOCH3 | " | Cr—ZrO2 (5/100) | " | " | 0.23 | 350 | 5.5 | 64 | 60*3 13*4 |
| 25 | p-CHO | " | Cr—ZrO2 (5/100) | benzene | 625 | 0.05 | " | 5.0 | 94 | 27 |

*1Y, R: structure shown

*2atomic ratio of specific element added with respect to the zirconium
*3Monoaldehyde selectivity
*4Dialdehyde selectivity While the invention has been described in detail and with reference to specific embodiments thereof, it will be apparent to one skilled in the art that various changes and modifications can be made therein without departing from the spirit and scope thereof.

What is claimed is:

1. A process for producing an aromatic aldehyde by catalytic hydrogenation of an aromatic carboxylic acid, wherein the improvement comprises using a catalyst comprising zirconium oxide containing as an essential component at least one element selected from the group consisting of chromium, manganese, iron, cobalt, zinc, lead, and indium.

2. A process according to claim 1, wherein said catalyst comprises zirconium oxide containing as an essential component at least one element selected from the group consisting of chromium, cobalt, iron, zinc, and indium.

3. A process according to claim 1, wherein said element contained as an essential component in the zirconium oxide is present in an atomic ratio of from about 0.001/1 to 0.5/1 with respect to the zirconium.

4. A process according to claim 1 wherein the hydrogenation is performed at a temperature in the range of from about 250° to 450° C.

5. A process according to claim 1, wherein the concentration of the aromatic carboxylic acid in the reaction system ranges from 0.1 to 10 vol% of the hydrogen volume.

6. A process according to claim 1, wherein said element contained as an essential component in the zirconium oxide is present in an atomic ratio of from 0.01/1 to 0.1/1 with respect to the zirconium.

7. A process according to claim 1, wherein the hydrogenation is performed at a temperature of from 300° to 400° C.

8. A process according to claim 1, wherein the concentration of the aromatic carboxylic acid in the reaction system ranges from 1 to 5 vol% of the hydrogen volume.

* * * * *